(12) United States Patent
Nappa et al.

(10) Patent No.: US 8,399,721 B2
(45) Date of Patent: *Mar. 19, 2013

(54) METHOD OF HYDRODECHLORINATION TO PRODUCE DIHYDROFLUORINATED OLEFINS

(75) Inventors: Mario Joseph Nappa, Newark, DE (US); Ekaterina N. Swearingen, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 523 days.

This patent is subject to a terminal disclaimer.

(21) Appl. No.: 12/641,875

(22) Filed: Dec. 18, 2009

(65) Prior Publication Data

US 2010/0160696 A1 Jun. 24, 2010

Related U.S. Application Data

(60) Provisional application No. 61/139,808, filed on Dec. 22, 2008.

(51) Int. Cl.
  *C07C 17/10* (2006.01)
  *C07C 17/00* (2006.01)
(52) U.S. Cl. .......................... 570/176; 570/155; 570/156
(58) Field of Classification Search .................. 570/176, 570/155, 156
See application file for complete search history.

(56) References Cited

U.S. PATENT DOCUMENTS

| | | | |
|---|---|---|---|
| 2,774,799 A | 12/1956 | Mantell et al. | |
| 2,802,887 A | 8/1957 | Miller et al. | |
| 2,900,423 A | 8/1959 | Smith | |
| 5,068,472 A | 11/1991 | Webster et al. | |
| 5,118,888 A | 6/1992 | Gervasutti et al. | |
| 5,243,103 A | 9/1993 | Lerot et al. | |
| 5,892,135 A | 4/1999 | Manogue et al. | |
| 2009/0012335 A1 | 1/2009 | Nappa et al. | |

FOREIGN PATENT DOCUMENTS

| | | |
|---|---|---|
| EP | 0053657 B1 | 4/1985 |
| EP | 0611745 A1 | 8/1994 |
| GB | 974612 | 11/1964 |
| JP | 05194286 A | 8/1993 |
| JP | 05215793 A | 8/1993 |
| WO | 90/08748 A1 | 8/1990 |
| WO | 95/05353 A1 | 2/1995 |
| WO | 9505353 A1 | 2/1995 |

OTHER PUBLICATIONS

Wong et al., Arene synthesis by extrusion reactions, ( Synthesis (1984), (9) , 787-90).*
Chemical Abstract, "Synthesis of Perfluoro-2-Butyne", Li, Zong-Zhen et al, Jan. 1, 1981, XP-002573948.
Heterogeneous Catalysis in Industrial Practice 2nd Edition, Satterfield, Chapter 4, McGraw-Hill, NY, 1991, pp. 87-112.
Journal of Catalysis, Boudar et al., vol. 81, 1983, pp. 204-213.
Wong et al., Arene Synthesis by Extrusion Reactions, Synthesis, 1984, 9, 787-790.

* cited by examiner

*Primary Examiner* — Jafar Parsa

(57) ABSTRACT

Disclosed is a process for the preparation of fluorine-containing olefins comprising contacting a chlorofluoroalkene with hydrogen in the presence of a catalyst at a temperature sufficient to cause replacement of the chlorine substituents of the chlorofluoroalkene with hydrogen to produce a fluorine-containing olefin, wherein said catalyst is a composition comprising chromium, nickel and optionally an alkali metal selected from potassium and cesium. Also disclosed are catalyst compositions for the hydrodechlorination of chlorofluoroalkenes comprising copper, nickel, and an alkali metal selected from potassium and cesium, and methods of making such catalysts.

20 Claims, No Drawings

METHOD OF HYDRODECHLORINATION TO PRODUCE DIHYDROFLUORINATED OLEFINS

CROSS REFERENCE(S) TO RELATED APPLICATION(S)

This application claims the benefit of priority of U.S. Provisional Applications 61/139,808, filed Dec. 22, 2008.

BACKGROUND INFORMATION

1. Field of the Disclosure

This disclosure relates in general to methods of synthesis of fluorinated olefins.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential.

SUMMARY

Disclosed is a process for the preparation of fluorine-containing olefins comprising contacting a chlorofluoroalkene with hydrogen in the presence of a catalyst at a temperature sufficient to cause replacement of the chlorine substituents of the chlorofluoroalkene with hydrogen to produce a fluorine-containing olefin, wherein said catalyst is a composition comprising chromium and nickel, and optionally an alkali metal selected from potassium and cesium. Also disclosed are processes for the preparation of fluorine-containing alkynes comprising contacting a chlorofluoroalkene with hydrogen in the gas phase in the presence of a catalyst at a temperature sufficient to cause elimination of the chlorine substituents of the chlorofluoroalkene to produce a fluorine-containing alkyne, wherein said catalyst is a composition comprising copper, nickel, optionally chromium and optionally an alkali metal. Also disclosed are catalyst compositions for the hydrodechlorination of chlorofluoroalkenes comprising copper, nickel, and an alkali metal selected from potassium and cesium, and methods of making such catalysts.

The foregoing general description and the following detailed description are exemplary and explanatory only and are not restrictive of the invention, as defined in the appended claims.

DETAILED DESCRIPTION

Disclosed are processes for the preparation of fluorine-containing olefins and fluorine-containing alkynes comprising contacting a chlorofluoroalkene with hydrogen in the presence of a catalyst at a temperature sufficient to cause replacement of the chlorine substituents of the chlorofluoroalkene with hydrogen to produce a fluorine-containing olefin, or elimination of the chlorine substituents of the chlorofluoroalkene to produce a fluorine-containing alkyne. Also disclosed are catalyst compositions for the hydrodechlorination of chlorofluoroalkenes comprising copper, nickel and an alkali metal selected from potassium and cesium, and methods of making such catalysts.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Before addressing details of embodiments described below, some terms are defined or clarified.

As used herein the term chlorofluoroalkene refers to compounds of the formula $R_fCCl=CClR_f$ wherein each $R_f$ is a perfluoroalkyl group independently selected from the group consisting of $CF_3$, $C_2F_5$, n-$C_3F_7$, i-$C_3F_7$, n-$C_4F_9$, i-$C_4F_9$ and t-$C_4F_9$. As used herein, the chlorofluoroalkenes referred to may be either the E-stereoisomer, the Z-stereoisomer, or any mixture thereof.

As used herein, the term fluorine-containing olefin refers to compounds of formula E- or Z—$R^1CH=CHR^2$, wherein each of $R^1$ and $R^2$ are, perfluoroalkyl groups independently selected from the group consisting of $CF_3$, $C_2F_5$, n-$C_3F_7$, i-$C_3F_7$, n-$C_4F_9$, i-$C_4F_9$ and t-$C_4F_9$.

As used herein, the term fluorine-containing alkyne refers to compounds of formula $R^1C\equiv CR^2$, wherein each of $R^1$ and $R^2$ are, perfluoroalkyl groups independently selected from the group consisting of $CF_3$, $C_2F_5$, n-$C_3F_7$, i-$C_3F_7$, n-$C_4F_9$, i-$C_4F_9$ and t-$C_4F_9$.

In one embodiment, the chlorofluoroalkene is 1,1,1,4,4,4-hexafluoro-2,3-dichloro-2-butene (CFC-1316mxx), and the fluorine-containing olefin is 1,1,1,4,4,4-hexafluoro-2-butene (HFC-1336mzz). In another embodiment, the chlorofluoroalkene is 1,1,1,4,4,5,5,5-octafluoro-2,3-dichloro-2-pentene (CFC-1418mxx), and the fluorine-containing olefin is 1,1,1,4,4,5,5,5-octafluoro-2-pentene. In yet another embodiment, the chlorofluoroalkene is 1,1,1,2,2,3,3,6,6,7,7,8,8,8-tetradecafluoro-4,5-dichloro-4-octene (CFC-171-14mccxx) and the fluorine-containing olefin is 1,1,1,2,2,3,3,6,6,7,7,8,8,8-tetradecafluoro-4-octene (HFC-173-14mcczz). In one embodiment, the chlorofluoroalkene is 1,1,1,4,4,4-hexafluoro-2,3-dichloro-2-butene (CFC-1316mxx), and the fluorine-containing alkyne is 1,1,1,4,4,4-hexafluoro-2-butyne.

Hydrogenation catalysts containing copper, nickel, chromium, palladium, and ruthenium are known in the art. They may be prepared by either precipitation methods or impregnation methods as generally described by Satterfield on pages 87-112 in *Heterogeneous Catalysis in Industrial Practice*, 2$^{nd}$ edition (McGraw-Hill, New York, 1991).

In one embodiment, catalytic compositions are employed comprising copper, nickel and/or chromium. Suitable components include halides such as CuF, CuCl, CuCl$_2$, CuClF, NiF$_2$, NiCl$_2$, NiClF, CrF$_3$, CrCl$_3$, CrCl$_2$F and CrClF$_2$; oxides such as CuO, NiO, and Cr$_2$O$_3$; and oxyhalides such as copper oxyfluoride and chromium oxyfluoride. Oxyhalides may be produced by conventional procedures such as, for example, halogenation of metal oxides. In one embodiment of a process to prepare fluorine-containing alkynes, catalytic compositions are employed comprising copper and nickel. In another embodiment of a process to prepare fluorine-containing alkynes, catalytic compositions are employed comprising copper, nickel and chromium. In another embodiment, of a process to produce fluorine-containing olefins, catalytic compositions are employed comprising nickel and chromium.

In some embodiments, the catalysts of this invention may contain other components, some of which are considered to improve the activity and/or longevity of the catalyst composition. Such catalysts include catalysts which are promoted with compounds of potassium, cesium, rubidium, or combinations thereof. Without wishing to be bound to any particular theory, alkali metal promoters are believed to reduce the rate of decline of catalyst activity over time.

The catalyst may be supported or unsupported. Supports such as metal fluorides, alumina and titania may be advantageously used. In one embodiment, the catalyst supports are fluorides of metals of Group II, including magnesium fluoride, calcium fluoride, strontium fluoride and barium fluoride. In one embodiment, the support is calcium fluoride. In one embodiment, a catalyst consists essentially of copper, nickel and chromium oxides (each of said oxides being preferably present in equimolar quantities) promoted with a potassium salt, on calcium fluoride.

In one embodiment, a catalyst contains proportionally about 1.0 mole CuO, about 0.2 to 1.0 mole NiO, about 1 to 1.2 moles $Cr_2O_3$ on about 1.3 to 2.7 moles $CaF_2$, promoted with about 1 to 20 weight %, based on the total catalyst weight, of an alkali metal selected from K, Cs, and Rb. In one embodiment, when K is the promoter, the amount is from about 2 to 20 weight percent of the total catalyst. In another embodiment, the amount of alkali metal is from about 5 to 15 weight percent. Without being bound by any particular theory, it is believed that additional of an alkali metal promoter to a catalyst composition for the production of fluorine-containing alkenes increases the selectivity for the production of the alkene, but at the same time reduces the overall conversion of starting material, especially at higher levels of alkali metal.

In one embodiment, the catalyst can be prepared by coprecipitating, from an aqueous medium, salts of copper, nickel and chromium (and optionally aluminum and zinc), with and on calcium fluoride; washing, heating and drying the precipitate. When alkali metal carbonates are used in the precipitation process to initially produce the corresponding insoluble copper, nickel or chromium carbonates, the alkali metal counter ion may be washed away in the washing step after the carbonates are precipitated.

After precipitation, washing and drying, the precipitated catalysts are calcined. Catalysts are calcined at temperatures from 375° C. to 650° C. In some embodiments, catalysts are calcined for from 2 hours to 16 hours. In other embodiments, catalysts are calcined for from 2 hours to 8 hours. In other embodiments, catalysts are calcined for from 2 hours to 4 hours.

In embodiments where an alkali metal promoter is desired, an alkali metal compound (e.g., KOH, KF, $K_2CO_3$ or $CsCO_3$ or Rb salt) is then deposited on the dried precipitate, prior to calcination to convert the copper, nickel and chromium to the respective oxides. Any soluble copper, nickel and chromium compound may be used. In one embodiment, the copper, nickel and chromium salts are chloride or nitrates. In another embodiment, the salts are nitrates. In one embodiment, promoters such as KOH, KF, $K_2CO_3$, $CsCO_3$ or Rb salt may be added prior to co-precipitation. In one embodiment, the promoter is provided from a mixture of more than one alkali metal compound.

In one embodiment, the catalyst is granulated, pressed into pellets, or shaped into other desirable forms. The catalyst may contain additives such as binders and lubricants to help insure the physical integrity of the catalyst during granulating or scraping the catalyst into the desired form. Suitable additives include carbon and graphite. When binders and/or lubricants are added to the catalyst, they normally, comprise about 0.1 to 5 weight percent of the weight of the catalyst.

In one embodiment, the catalyst is activated prior to use by treatment with hydrogen, air, or oxygen at elevated temperatures. After use for a period of time in the process of this invention, the activity of the catalyst may decrease. When this occurs, the catalyst may be reactivated by treating it with hydrogen, air or oxygen, at elevated temperature in the absence of organic materials.

In one embodiment, the molar ratio of copper:nickel:alkali metal selected from potassium and cesium in the copper/nickel/potassium catalyst is from about 0.1 to about 0.9 copper, from about 0.1 to about 0.9 nickel, and from about 0.01 to about 0.3 potassium. In one embodiment, the molar ratio of copper:nickel:potassium in the copper/nickel/potassium catalyst is 0.5:0.4:0.1. In another embodiment, the molar ratio is 0.45:0.45:0.1. In yet another embodiment, the molar ratio is 0.3:0.6:0.1. In yet another embodiment, the molar ratio is 0.3:0.5:0.2. In yet another embodiment, the molar ratio is 0.5:0.45:0.05. In one embodiment, the weight ratio of total catalyst material to support material may be from about 1:2 to about 2:1.

In embodiments of catalyst comprising chromium and nickel, the molar ratio of chromium to nickel is from 1:9 to 9:1. In other embodiments, the molar ratio of chromium to nickel is from 1:3 to 3:1. In yet other embodiments, the molar ratio of chromium to nickel is from 1:2 to 2:1.

In one embodiment, the contact time for the process ranges from about 2 to about 120 seconds.

In one embodiment, the ratio of hydrogen to chlorofluoroalkene is from about 1:1 to about 7.5:1. In another embodiment, the ratio of hydrogen to chlorofluoroalkene is from about 1:1 to about 5:1. In another embodiment, the ratio of hydrogen to chlorofluoroalkene is from about 5:1 to about 20:1.

In one embodiment, the process for preparation of fluorine-containing olefins and fluorine-containing alkynes comprises reacting a chlorofluoroalkene with hydrogen in a reaction vessel constructed of an acid resistant alloy material. Such acid resistant alloy materials include stainless steels, high nickel alloys, such as Monel, Hastelloy, and Inconel. In one embodiment, the reaction takes place in the vapor phase.

In one embodiment, the temperature at which the process is run may be a temperature sufficient to cause replacement of the chlorine substituents with hydrogen over a suitable catalyst. In another embodiment, the process is conducted at a temperature of from about 100° C. to about 450° C. Within this temperature range, it is expected that different catalysts will require somewhat different temperatures. In one embodiment of a process to produce fluorine-containing alkynes over a catalyst composition comprising nickel and copper, the process is conducted at a temperature of at least 350° C.

In some embodiments, the pressure for the hydrodechlorination reaction is not critical. In other embodiments, the process is performed at atmospheric or autogenous pressure. Means may be provided for the venting of the excess pressure of hydrogen chloride formed in the reaction and may offer an advantage in minimizing the formation of side products. Additional products of the reaction may include partially hydrodechlorinated intermediates; saturated hydrogenated compounds; various partially chlorinated intermediates or saturated compounds; and hydrogen chloride (HCl). For example, wherein the chlorofluoroalkene is 2,3-dichloro-1,1, 1,4,4,4-hexafluoro-2-butene (CFC-1316mxx, E- and/or Z-isomers), the compounds formed in addition to E- and/or Z-1,1,1,4,4,4-hexafluoro-2-butene (E- and/or Z-HFC-1336mzz) may include, 1,1,1,4,4,4-hexafluorobutane (HFC-356mff), pentafluorobutane (HFC-1345, different isomers), 2-chloro-1,1,1,4,4,4-hexafluorobutane (HFC-346mdf), E and/or Z-2-chloro-1,1,1,4,4,4-hexafluoro-2-butene (E- and/or Z-HCFC-1326mxz), and 1,1,1,4,4,4-hexafluoro-2-butyne (HFB). In some embodiments when the starting chlorofluoroalkene is 2,3-dichloro-1,1,1,4,4,4-hexafluoro-2-butene, 1,1,1,4,4,4-hexafluoro-2-butyne is the majority product.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

In the examples the follow abbreviations or codes may be used:

CT=contact time
t-1336=E-1336mzz=E-$CF_3CH$=$CHCF_3$
c-1336=Z-1336mzz=Z-$CF_3CH$=$CHCF_3$
356mff =$CF_3CH_2CH_2CF_3$
1345=$C_4H_3F_5$
346mdf=$CF_3CHClCH_2CF_3$
1326=E- and/or Z-$CF_3CH$=$CClCF_3$
t-1326mxz=Z-1326mxz=Z-$CF_3CH$=$CClCF_3$
c-1326mxz=E-1326 mxz=E-$CF_3CH$=$CClCF_3$
1316mxx=E/Z-$CF_3CCl$=$CClCF_3$
t-1316mxx=E-1316mxx=E-$CF_3CCl$=$CClCF_3$
c-1316mxx=Z-1316mxx=Z-$CF_3CCl$=$CClCF_3$
1418mxx=E/Z-$CF_3CCl$=$CClCF_2CF_3$
1438mzz=E/Z-$CF_3CH$=$CHCF_2CF_3$
171-14mccxx=E/Z-$CF_3CF_2CF_2CCl$=$CClCF_2CF_2CF_3$
173-14mcczz=E/Z-$CF_3CF_2CF_2CH$=$CHCF_2CF_2CF_3$
t-172-14=E-$CF_3CF_2CF_2CCl$=$CHCF_2CF_2CF_3$
c-172-14=Z-$CF_3CF_2CF_2CCl$=$CHCF_2CF_2CF_3$
HFB=$CF_3C$≡$CCF_3$

Example 1

Example 1 describes the preparation of a catalyst comprising copper, nickel and potassium.

Solutions of 172.5 g (0.72 mole) of $Cu(NO_3)_2.4H_2O$ dissolved in 375 ml of water, and 218.25 g (0.625 mole) of $Ni(NO_3)_2.6H_2O$ dissolved in 375 ml $H_2O$, were mixed together and then added to 261 g (3.3 mole) of $NH_4HCO_3$ dissolved in 3 L $H_2O$. The resulting slurry was stirred for 1 hr, allowed to settle overnight and filtered (paper filter). The solids were placed in a beaker with 2 L of water, stirred and filtered again. The mixed carbonates were dried in vacuum at 90° C. for 24 hrs. Then, they were crushed. That gave 219 g of $CuCO_3/NiCO_3$. A solution of 22 g of $K_2CO_3$ dissolved in 130 ml of water was prepared. This solution was poured into the mixture of $CuCO_3/NiCO_3$. The resulting mixture was dried in an oven at 90° C. with occasional stirring. Then the sample was calcined in air at 400° C. for 2 hrs. Inductively coupled plasma mass spectrometry showed following content of 11.2% K, 27.2% Ni and 34.7% Cu.

Example 2

Example 2 describes the preparation of a catalyst comprising copper, nickel, chromium and potassium on calcium fluoride.

Aqueous calcium nitrate (2.7 moles) was mixed with aqueous potassium fluoride (5.4 moles), heated, and stirred briefly at 100° C. to form a slurry of $CaF_2$. To this slurry was added copper nitrate (1 mole), nickel nitrate (1 mole) and chromium nitrate (1 mole) as solids. The slurry was stirred at 70 to 80° C. until the salts, other than $CaF_2$, dissolve. This was followed by adding 0.1 mole of KOH as aqueous potassium hydroxide over 1 hour and boiling the mixture briefly. The slurry was cooled to 40 to 50° C. and filtered. The solid was washed exhaustively to reduce the potassium content to an undetectable level. After drying, potassium hydroxide was added as a solution in quantities sufficient to provide a catalyst containing 9 weight % potassium. After drying again, the catalyst was calcined at 600° C. for 8 to 16 hours, then granulated and screened to 1 to 2 mm particles. The catalyst was mixed with 1 to 5 wt % "Sterotex" powdered lubricant (registered trademark of Capital City Products Co., Columbus Ohio, division of Stokely-Van Camp, for its edible hydrogenated vegetable oil) to give ⅛"×⅛" (3.2 mm×3.2 mm) cylindrical pellets from a Stokes tablet machine.

Example 3

Example 3 describes the preparation of a catalyst comprising copper, nickel and potassium on calcium fluoride.

A solution of 94 of $KF.2H_2O$ in 500 ml of $H_2O$ was added to a solution of 118 g of $Ca(NO_3)_2.4H_2O$ in 500 ml of $H_2O$ to form a slurry. To this slurry was added a solution containing 116.5 g of $Cu(NO_3)_2*2.5H_2O$ and 145.5 g of $Ni(NO_3)_2.6H_2O$, in 1 L of water. After stirring the resulting slurry, a solution of 176 g of $NH_4HCO_3$ dissolved in 1 L of water was added. After stirring, the resulting filter cake was washed with 5 L of water and then dried at 120° C. The dried material was crushed to 20 mesh, providing 130.9 g of powder. 13.2 g of $K_2CO_3$ were dissolved in 75 ml of water and added to the powder with stirring. Then the beaker was placed in a drying oven. The catalyst was stirred every 30-45 min until it dried. Then the powder was calcined in air at 400° C. for 2 hours. The powder was pressed and pelletized.

Example 4

Example 4 demonstrates the preparation of a catalyst comprising copper, nickel and cesium.

172.5 gm (0.72 mole) of $Cu(NO_3)_2 \cdot 4H_2O$ was dissolved in 375 ml of water, 218.25 (0.625 mole) of $Ni(NO_3)_2 \cdot 6H_2O$ was dissolved in 375 ml $H_2O$. These two solutions were mixed together and added to a solution of 261 g (3.3 mole) of $NH_4HCO_3$ dissolved in 3 L $H_2O$. The resulting slurry was stirred for 1 hr and allowed to settle overnight, then filtered (paper filter). The solids were placed in a beaker with 2 L of water, stirred and filtered again. The solids were dried in vacuum at 90° C. for 24 hrs, then crushed. This produced about 220 g of $CuCO_3/NiCO_3$.

40 g of $Cs_2CO_3$ were dissolved in 125 ml of water. This solution was stirred into the 220 g of $CuCO_3/NiCO_3$. The wet mixture was placed into oven and was dried with occasional stirring. The resulting solid was crushed, and calcined at 400° C.

Example 5

Example 5 demonstrates the conversion of CFC-1316mxx to HFC-1336mzz over K/Ni/Cu.

An inconel tube (⅝ inch OD) was filled with 6 cc (9.51 gm) of the K/Ni/Cu catalyst of Example 1 which had been crushed and sieved to 12/20 mesh. The catalyst was treated with hydrogen (up to 20 sccm, $3.3 \times 10^{-7}$ $m^3$) for 4.0 hours at 260° C. and then for 16.5 hours at 350° C. The temperature was lowered to 325° C., and the hydrogen was then lowered to 8.8 sccm ($3.3 \times 10^{-8}$ $m^3$). CFC-1316mxx was fed at 0.44 ml/hour through a vaporizer set at 89° C., providing a total contact time of about 29 seconds. After 24 hours of operation, the conversion of CFC-1316mxx was about 41%, with a selectivity for Z-2,3-dihydrohexafluoro-2-butene of 75%. A major co-product was hexafluoro-2-butyne, which can be recycled and converted to the desired product. Including the butyne, the selectivity was about 90% for Z-2,3-dihydrohexafluoro-2-butene.

These conditions were maintained for a run of 202 hours, after which the conversion dropped to about 19%. At this point the catalyst was regenerated with air, as indicated in Table 1, at 300° C.

TABLE 1

| Minutes | Air (sccm) | N2 (sccm) |
|---|---|---|
| 15 | 0 | 50 |
| 15 | 2.5 | 45 |
| 15 | 5 | 45 |
| 15 | 10 | 40 |
| 15 | 20 | 30 |
| 15 | 30 | 20 |
| 15 | 40 | 10 |

TABLE 1-continued

| Minutes | Air (sccm) | N2 (sccm) |
|---|---|---|
| 15 | 40 | 5 |
| 60 | 40 | 0 |

The catalyst was treated with hydrogen as described initially, and the temperature was set to 325° C. The hydrogen flow rate was then adjusted to 8.8 sccm ($3.3 \times 10^{-8}$ $m^3$). CFC-1316mxx was fed at 0.44 ml/hour through a vaporizer set at 89° C. using a sweep of $N_2$ of 2.4 sccm ($4.0 \times 10^{-8}$ $m^3$). After 23 hours of operation, the conversion of CFC-1316mxx was about 35%, with a selectivity for Z-2,3-dihydrohexafluoro-2-butene of 75% and an overall selectivity (including the butyne) of 88%. This catalyst was run for 378 hours including two regenerations. During the course of this run, the rate of butyne formation showed a $2.9 \times 10^{-4}$ percent increase per hour, apparently an indication of the rate of decline of catalyst activity.

Example 6

Example 6 demonstrates the conversion of CFC-1316mxx to HFC-1336mzz over K/Ni/Cu.

An Inconel tube (⅝ inch OD) was filled with 8 cc (12.95 gm) of the K/Ni/Cu catalyst from Example 1, which had been crushed and sieved to 12/20 mesh. The catalyst was treated with hydrogen (up to 20 sccm, $3.3 \times 10^{-7}$ $m^3$) for 4.0 hours at 260° C. and then for 16.5 hours at 350° C. The temperature was then lowered to 325° C., and the hydrogen flow rate was then lowered to 8.8 sccm ($3.3 \times 10^{-8}$ $m^3$). CFC-1316mxx was then fed at 0.19 ml/hour through a vaporizer set at 89° C., providing a total contact time of about 60 seconds. After 24 hours of operation, the conversion of CFC-1316mxx was about 27%, with a selectivity for Z-2,3-dihydrohexafluoro-2-butene of 72%. Very little hexafluoro-2-butyne was formed under these conditions. After 266 hours of operation at these conditions without an air regeneration, the conversion of CFC-1316mxx was 13%, with a selectivity for Z-2,3-dihydrohexafluoro-2-butene of 82%. During the course of this run, the rate of butyne formation showed an $8.0 \times 10^{-6}$ percent increase per hour, which appears to be an indication of the rate of decline of catalyst activity.

Example 7

Example demonstrates the conversion of CFC-1316mxx to HFC-1336mzz over Cs/Ni/Cu.

A Hastelloy tube (0.625" OD×0.576 ID×10"L) was filled with 11 cc of the catalyst of Example 4, which had been pelletized to 12/20 mesh. The packed portion of the reactor was heated by a 5.0"×1" ceramic band heater clamped to the outside of the reactor. A thermocouple, positioned between the reactor wall and the heater, measured the reactor temperature. The catalyst was activated in the reactor by heating the reactor to 26° C. for 30 minutes under a 20 sccm ($3.33 \times 10^{-7}$ m3/s) flow of nitrogen. The flow of nitrogen was then gradually (within 3 hrs) decreased while a flow of hydrogen was increased to 20 sccm ($3.33 \times 10^{-7}$ m3/s). The hydrogen flow was maintained at 20 sccm ($3.33 \times 10^{-7}$ m3/s), and the reactor was heated to 350° C. These conditions were maintained overnight (~16 hours). The reactor was then cooled to 250° C. immediately prior to testing.

The hydrodechlorination of 1316mxx was studied at a temperature range of 275-325° C., with a contact time of 30 seconds and a ratio of hydrogen to 1316mxx of 7:1. The products of the reaction were analyzed by GCMS to give the molar concentrations as listed in Table 2.

TABLE 2

| H2/1316 ratio | Contact Time, sec | Temp ° C. | Hexafluoro Butyne | t-1336 | c-1336 | t-1326mxz | t-1316mxx | c-1316mxx |
|---|---|---|---|---|---|---|---|---|
| 7:1 | 30 | 275 | 15.9 | 0.24 | 19.2 | 6.0 | 31.75 | 25.5 |
| 7:1 | 30 | 325 | 38.8 | 0.94 | 25.7 | 5.41 | 14.5 | 13.7 |

Example 8 K/Cu/Ni/CaF$_2$

Solutions of Ca(NO$_3$)$_2$.4H$_2$O [(134.5 g, 0.57 moles) dissolved in 757 ml of H$_2$O] and KF.2H$_2$O [(108.1 g, 1.15 moles) dissolved in 757 ml of H$_2$O] were added simultaneously to a reaction vessel containing 1419 ml of water to form a slurry. After 30 minutes of stirring, solutions of Ni(NO$_3$)$_2$.6H$_2$O (154.9 g, 0.53 moles) and Cu(NO$_3$).2.5H$_2$O (121.7 g, 0.52 moles) in 1000 ml of water, and K$_2$CO$_3$(200 g, 1.45 moles) in 1419 ml of water, were added simultaneously to the slurry.

The slurry was filtered and washed twice with 5 L of water. The filter cake was then dried in an oven. The dried cake was then calcined for 2 hrs at 375° C. and 119 g of the catalyst were obtained. Graphite (M-970) (5 g) was added to the catalyst and it was calcined at 650° C. for 2 hrs.

KF (9.7 g) was dissolved in 30 ml of water. This solution was mixed with 65 g of the catalyst prepared above. The mixture was placed in an oven where it was dried with occasional stirring.

The catalyst was then reduced in a quartz boat. The catalyst was placed in a quartz tube, which was then purged with 500 sccm N$_2$ for 30 min, followed by 100 sccm of He 30 min, all at room temperature. The catalyst was then heated to 260° C. at a rate of 5° C. per minute. At 260° C., the He:H$_2$ ratio was changed from 100:0 to 0:100 in 10% increments every 10 min. The sample was then heated at to 400° C. at a rate of 5° C. per minute, and maintained at these conditions for 4 hours. After cooling in flowing H$_2$, the sample was purged with 500 sccm N$_2$ and passivated in N$_2$/O$_2$, with the flow rate of O$_2$ raised from 1% to 5% while maintaining the temperature below 30° C.

The hydrogenation data for the catalyst is summarized in Table 3.

Example 9 Cr/Ni/Cu/CaF$_2$

Solutions of Ca(NO$_3$)$_2$.4H$_2$O [(250 g, 1.06 moles) dissolved in 757 ml of H$_2$O] and KF.2H$_2$O [(122.5 g, 2.11 moles) of dissolved in 757 ml of H$_2$O] were added simultaneously to a reaction vessel containing 1419 ml of water to make a slurry. After 30 minutes of stirring, solutions of Cr(NO$_3$)$_3$.9H$_2$O (362 g (0.905 mole), Ni(NO$_3$)$_2$.6H$_2$O (154.9 g, 0.53 moles) and Cu(NO$_3$).2.5H$_2$O (121.7 g, 0.52 moles) in 1000 ml of water, and K$_2$CO$_3$[(453.6 g, 3.29 moles) in 1419 ml] of water were added simultaneously to the slurry.

The slurry was filtered, then washed 2 times with 5 L of water. The filter cake was dried in an oven, then the cake was calcined for 2 hrs at 375° C. 283 g of the catalyst were obtained. Graphite (M-970) (11.3 g) was added to the catalyst and it was calcined again at 650° C. for 2 hrs.

The catalyst was then reduced in a quartz boat. The catalyst was placed in a quartz tube, and was purged with 500 sccm N$_2$ for 30 minutes, and then purged with 100 sccm of He for 30 minutes, all at room temperature. The sample was then heated to 260° C. at a rate of increase of 5° C. per minute. At 260° C. the He:H$_2$ ratio was changed from 100:0 to 0:100 in 10% increments every 10 minutes. The sample was then heated at a rate of 5° C. per minute to 400° C., and maintained under hydrogen at these conditions for 4 hours. After cooling in flowing H$_2$, the sample was purged with 500 sccm N$_2$ and passivated in N$_2$/O$_2$, with the percentage of O$_2$ being slowly raised from 1% to 5% while keeping the temperature below 30° C.

The hydrogenation data is summarized in Table 3.

Example 10 K/Cu/Ni/Cr

Solutions of Cr(NO$_3$)$_3$.9H$_2$O (362 g (0.905 mole), Ni(NO$_3$)$_2$6.H$_2$O (154.9 g, 0.53 moles) and Cu(NO$_3$).2.5H$_2$O (121.7 g, 0.52 moles) in 1000 ml of water, and K$_2$CO$_3$(453.6 g, 3.29 moles) in 1419 ml of water, were added to a reaction vessel containing 700 ml of water. The slurry was filtered, washed twice with 5 L of water. The filter cake was then dried in an oven, then calcined for 2 hours at 650° C. 249 g of the catalyst were obtained. Graphite (M-970) (10 g) was then added to the catalyst and it was calcined again at 650° C. for 2 hours.

The catalyst was then reduced in a quartz boat. The catalyst was added to a quartz tube and the sample was purged with 500 sccm N$_2$ for 30 min, then with 100 sccm of He for 30 min, all at room temperature. The sample was then heated 5° C. per minute to 260° C. At 260° C., the He:H$_2$ ratio was changed from 100:0 to 0:100 in 10% increments every 10 minutes. The sample was then heated 5° C. per minute to 400° C., and maintained under hydrogen at these conditions for 4 hours. After cooling under flowing H$_2$, the sample was purged with 500 sccm N$_2$ and passivated with N$_2$/O$_2$, with the percentage of O$_2$ being slowly raised from 1% to 5%, while keeping the temperature below 30° C.

The hydrogenation data for this catalyst is summarized in Table 3.

Example 11 K/Cu/Ni/CaF$_2$

This catalyst was obtained from Johnson Matthey Corp and contained about 10% K and a ratio of Cu/Ni of about 1:1 on a calcium fluoride support.

The hydrogenation data for this catalyst is summarized in Table 3.

Example 12 K/Cr/Ni/Cu/CaF$_2$

This catalyst was obtained from BASF Corp. and contained about 10% K and a ratio of Cu/Ni/Cr of about 1:1:2 on a calcium fluoride support.

The hydrogenation data for this catalyst is summarized in Table 3.

Example 13 K/Ni/Cr/CaF$_2$

Solutions of Ca(NO$_3$)$_2$.4H$_2$O (250 g, 1.06 moles) dissolved in 757 ml of H$_2$O and KF.2H$_2$O (122.5 g, 2.11 moles) of dissolved in 757 ml of H$_2$O were added simultaneously to a reaction vessel containing 1419 ml of water. After 30 minutes of stirring, solutions of Cr(NO$_3$)$_3$.9H$_2$O (362 g (0.905 mole) and Ni(NO$_3$)$_2$.6H$_2$O (309.8 g, 1.06 moles) in 1000 ml of water, and $K_2CO_3$ (453.6 g, 3.29 moles) in 1419 ml of water were added simultaneously to the slurry.

The slurry was filtered and washed twice with 5 L of water. The filter cake was dried in an oven, then calcined for 2 hours at 375° C. 252 g of the catalyst were obtained. Graphite (M-970) (10 g) was added to the catalyst and it was calcined again at 1000° C. for 2 hours.

The catalyst was then reduced in a quartz boat. The catalyst was placed in a quartz tube, which was purged with 500 sccm $N_2$ for 30 minutes and then 100 sccm of He for 30 minutes, all at room temperature. The sample was heated 5° C. per minute to 260° C. At 260° C., the He:$H_2$ ratio was changed from 100:0 to 0:100 in 10% increments every 10 minutes. The sample was then heated 5° C. per minute to 400° C., and maintained at these conditions for 4 hours. After cooling in flowing $H_2$, the sample was purged with 500 sccm $N_2$ and passivated in $N_2/O_2$ within the $O_2$ being slowly raised from 1% to 5%, while keeping the temperature below 30° C.

The hydrogenation data for this catalyst is summarized in Table 3.

Example 14 K/Ni/Cr

Solutions of $Cr(NO_3)_3.9H_2O$ (362 g (0.905 mole) and $Ni(NO_3)_2.6H_2O$ (309 g, 1.06 moles) in 1500 ml of water, and $K_2CO_3$(453.6 g, 3.29 moles) in 1419 ml of water, were added to a reaction vessel containing 700 ml of water. The resulting slurry was filtered and washed twice with 5 L of water. The filter cake was then dried in an oven, and calcined for 2 hours at 375° C. 170 g of the catalyst were obtained. Graphite (M-970) (6.83 g) was added to the catalyst and it was again calcined at 650° C. for 2 hours.

The catalyst was then reduced in a quartz boat. The catalyst was placed in a quartz tube. The sample was purged with 500 sccm $N_2$ for 30 min and then 100 sccm of He 30 min, all at room temperature. The sample was heated to 260° C. at a rate of 5° C. per minute. At 260° C., the He:$H_2$ ratio was changed from 100:0 to 0:100 in 10% increments every 10 minutes. The sample was then heated at a rate of 5° C. per minute to 400° C., and maintained under this temperature and under hydrogen for 4 hours. After cooling in flowing $H_2$, the sample was purged with 500 sccm $N_2$ and passivated in $N_2/O_2$, with the $O_2$ level being slowly raised from 1% to 5%, while keeping the temperature below 30° C.

The hydrogenation data for this catalyst is summarized in Table 3.

Example 15 Cu/Ni/CaF$_2$

This catalyst was obtained from Johnson Matthey Corp and contained a ratio of Cu/Ni of about 1:1 on a calcium fluoride support. The hydrogenation data for this catalyst is summarized in Table 3.

Example 16 Cs/Cu/Ni/CaF$_2$

This catalyst was obtained from Johnson Matthey Corp and contains about 10% Cs, and a ratio of Cu/Ni of about 1:1 on a calcium fluoride support.

The hydrogenation data is summarized in Table 3.

Example 17 K/Ni/Cu

Solutions of $Ni(NO_3)_2.6H_2O$ (232 g, 0.79 moles) and $Cu(NO_3)_2.2.5H_2O$ (182.5 g, 0.79 moles) in 1000 ml of water, and $K_2CO_3$ (300 g, 2.175 moles) in 2000 ml of water, were added simultaneously to a reaction vessel containing 1000 ml of water.

The resulting slurry was filtered and washed twice with 5 L of water. The filter cake was then dried in an oven, and then calcined for 2 hours at 375° C. 124 g of the catalyst were obtained. Graphite (M-970) (5 g) was added to the catalyst and it was calcined again at 650° C. for 2 hours.

KF (11 g) was dissolved in 30 ml of water and added with stirring to 75 g of the catalyst prepared above. The mixture was placed in an oven where it was dried with occasional stirring at 100° C.

The catalyst was then reduced in a quartz boat. The catalyst was placed in a quartz tube, and purged with 500 sccm $N_2$ for 30 minutes, and then with 100 sccm of He for 30 minutes, all at room temperature. The sample was then heated to 260° C. at a rate of 5° C. per minute. At 260° C., the He:$H_2$ ratio was changed from 100:0 to 0:100 in 10% increments every 10 minutes. The sample was then heated at a rate of 5° C. per minute to 400° C., and maintained at this temperature and under hydrogen for 4 hours. After cooling in flowing $H_2$, the sample was purged with 500 sccm $N_2$ and passivated in $N_2/O_2$, with the $O_2$ level being slowly raised from 1% to 5%, while keeping the temperature below 30° C.

The hydrogenation data for this catalyst is summarized in Table 3.

Example 18 Cr/Ni

A sample of commercial Chrome-Nickel catalyst obtained from AOA Maxam-Chirchiq.

The hydrogenation data for this catalyst is summarized in Table 4.

Example 19 K/Cr/Ni 6.5 g of KF was dissolved in 25 ml of water and added to 42 g of commercial Chrome-Nickel catalyst obtained from AOA Maxam-Chirchiq (see Example 18) with stirring. The mixture was dried overnight at 100° C. with occasional stirring. The catalyst was then reduced.

The hydrogenation data for this catalyst is summarized in Table 4.

Example 20 K/Cr/Ni

Following the procedure of Example 19, 50 g of ChromeNickel catalyst was impregnated with 15 g of KF and reduced.

The hydrogenation data for this catalyst is summarized in Table 4.

Example 21. K/Cr/Ni

Following the procedure of Example 19, 50 g of ChromeNickel catalyst was impregnated with 3.75 g of KF and reduced.

The hydrogenation data for this catalyst is summarized in Table 4.

Example 22 Cu/Ni/Cr/CaF$_2$

Solutions of $Ca(NO_3)_2.4H_2O$ [(317.7 g, 1.347 moles) dissolved in 757 ml of $H_2O$], and $KF.2H_2O$ [(155.6 g, 2.7 moles) of dissolved in 757 ml of $H_2O$] were added simultaneously to a reaction vessel containing 1419 ml of water. After 30 minutes of stirring, solutions of $Cr(NO_3)_3.9H_2O$ (362 g (0.905 mole), $Ni(NO_3)_2.6H_2O$ (309.8 g, 1.06 moles) and $Cu(NO_3)_2.2.5H_2O$ (182.5 g, 0.79 moles) in 1500 ml of water, and $K_2CO_3$(508 g, 4 moles) in 1419 ml of water, were added simultaneously to the resulting slurry.

The slurry was filtered and washed twice with 5 L of water. The filter cake was dried in an oven, then the cake was calcined for 2 hours at 375° C. 390 g of the catalyst were obtained. Graphite (M-970) (15.6 g) was added to the catalyst and it was calcined at 650° C. for 2 hours.

The catalyst was then reduced in a quartz boat. The catalyst was placed in a quartz tube, and purged with 500 sccm $N_2$ for 30 minutes, and then purged with 100 sccm of He for 30 minutes, all at room temperature. The sample was then heated to 260° C. at a rate of 5° C. per minute. At 260° C., the He:$H_2$ ratio was changed from 100:0 to 0:100 in 10% increments every 10 minutes. The sample was then heated at a rate of 5° C. per minute to 400° C., and maintained at this temperature and under hydrogen for 4 hours. After cooling in flowing $H_2$, the sample was purged with 500 sccm $N_2$ and passivated in $N_2/O_2$, with the $O_2$ level being slowly raised from 1% to 5%, while keeping the temperature below 30° C.

The hydrogenation data for this catalyst is summarized in Table 3.

Example 23 K/Cu/Ni/Cr/CaF$_2$ 100 g of a catalyst prepared in Example 22 was impregnated with 12 g of KF before reduction, and then reduced as described in Example 22.

The hydrogenation data for this catalyst is summarized in Table 3.

Example 24 Cu/Ni/Cr

Solutions of $Cr(NO_3)_3 \cdot 9H_2O$ (362 g (0.905 mole), $Ni(NO_3)_2 \cdot 6H_2O$ (309 g, 1.06 moles) and $Cu(NO_3)_2 \cdot 2.5H_2O$ (21.7, 0.52 moles) in 1500 ml of water, and $K_2CO_3$ (508 g, 4 moles) in 1419 ml of water, were added to a reaction vessel containing 1419 ml of water. The resulting slurry was filtered, and washed twice with 5 L of water. The filter cake was dried in an oven and then it was calcined for 2 hours at 375° C. 294 g of the catalyst were obtained. Graphite (M-970) (11.76) was added to the catalyst and it was calcined again at 650° C. for 2 hours.

The catalyst was then reduced in a quartz boat. The catalyst was placed in a quartz tube, and purged with 500 sccm $N_2$ for 30 minutes, and then purged with 100 sccm of He for 30 minutes, all at room temperature. The sample was then heated to 260° C. at a rate of 5° C. per minute. At 260° C., the He:$H_2$ ratio was changed from 100:0 to 0:100 in 10% increments every 10 minutes. The sample was then heated at a rate of 5° C. per minute to 400° C., and maintained at this temperature and under hydrogen for 4 hours. After cooling in flowing $H_2$, the sample was purged with 500 sccm $N_2$ and passivated in $N_2/O_2$, with the $O_2$ level being slowly raised from 1% to 5%, while keeping the temperature below 30° C.

The hydrogenation data for this catalyst is summarized in Table 3.

Example 25 K/Ni/Cu

This catalyst was obtained from Johnson Matthey Corp and contained about 5% K, and a ratio of Cu/Ni of about 1:1.

The hydrogenation data for this catalyst is summarized in Table 3.

Conversions of CFC-1316mxx to Hexafluorobutyne

An inconel tube (⅝ inch OD) was filled with 4 cc of catalyst that had been crushed and sieved to 12/20 mesh. The following general procedure was used to activate all of the catalysts. The temperature of the catalyst bed was raised to 260° C. and purged with nitrogen (20 sccm, $3.3 \times 10^{-7}$ m$^3$/sec) for 30 minutes. Then the flow of nitrogen was reduced to 10 sccm ($1.7 \times 10^{-7}$ m$^3$/sec) and $H_2$ was fed at 10 sccm ($1.7 \times 10^{-7}$ m$^3$/sec) for 15 minutes. The flow of nitrogen was then lowered to 8 sccm ($1.3 \times 10^{-7}$ m$^3$/sec) and the flow of $H_2$ was raised to 12 sccm ($2.0 \times 10^{-7}$ m$^3$/sec) for 15 minutes. The flow of nitrogen was then lowered to 6 sccm ($1.0 \times 10^{-7}$ m$^3$/sec) and the flow of $H_2$ was raised to 14 sccm ($2.3 \times 10^{-7}$ m$^3$/sec) for 15 minutes. The flow of nitrogen was then lowered to 4 sccm ($6.7 \times 10^{-8}$ m$^3$/sec) and the flow of $H_2$ was raised to 16 sccm ($2.7 \times 10^{-7}$ m$^3$/sec) for 15 minutes. The flow of nitrogen was then lowered to 2 sccm ($3.3 \times 10^{-8}$ m$^3$/sec) and the flow of $H_2$ was raised to 18 sccm ($3.0 \times 10^{-7}$ m$^3$/sec) for 15 minutes. The flow of nitrogen was then discontinued and the flow of $H_2$ was raised to 20 sccm ($3.3 \times 10^{-7}$ m$^3$/sec) for 15 minutes. The temperature was then raised to 400° C. and the flows continued for an additional 120 minutes. After this activation period, the catalyst bed temperature was changed to reaction conditions specified in the tables below.

The data in the table below were obtained at a $H_2$/1316 mxx ratio of 3.9 and a contact (calculated at 25° C.) of 20 seconds. Part of the reactor effluent was passed through a series of valves and analyzed by GCMS. The following table is an average of the last five injections from 13-17 hours of continuous operation at this condition.

TABLE 3

Synthesis of Hexafluoro-2-Butyne

| Example | 1316mxx Conv | Sel Z-1336 | Sel Butyne | Sel E-1336 | Sel E, Z-1326 | Temp °C. |
|---|---|---|---|---|---|---|
| 8 | 38% | 9% | 80% | 0% | 5% | 398 |
| 9 | 32% | 3% | 68% | 1% | 10% | 402 |
| 10 | 36% | 4% | 66% | 1% | 11% | 399 |
| 11 | 42% | 10% | 75% | 1% | 5% | 401 |
| 12 | 45% | 5% | 71% | 1% | 8% | 406 |
| 13 | 47% | 22% | 53% | 2% | 8% | 398 |
| 14 | 52% | 29% | 36% | 2% | 7% | 401 |
| 15 | 54% | 12% | 74% | 1% | 6% | 400 |
| 16 | 25% | 10% | 63% | 3% | 7% | 398 |
| 17 | 47% | 10% | 74% | 1% | 7% | 400 |
| 22 | 31% | 4% | 65% | 1% | 14% | 400 |
| 23 | 36% | 4% | 63% | 1% | 13% | 401 |
| 24 | 26% | 2% | 64% | 1% | 17% | 400 |
| 25 | 45% | 10% | 73% | 1% | 10% | 399 |

TABLE 4

Synthesis of 1,1,1,3,3,3-hexafluoro-2-butene

| Example | 1316mxx Conv | Sel Z-1336 | Sel Butyne | Sel E-1336 | Sel E, Z-1326 | Temp °C. | % K |
|---|---|---|---|---|---|---|---|
| 18 | 90% | 33% | 2% | 5% | 8% | 401 | 0% |
| 21 | 99% | 64% | 0% | 7% | 6% | 399 | 5% |
| 19 | 67% | 68% | 1% | 7% | 8% | 400 | 10% |
| 20 | 40% | 71% | 1% | 6% | 10% | 399 | 20% |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below.

Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, any reference to values stated in ranges includes each and every value within that range.

What is claimed is:

1. A process for the preparation of fluorine-containing olefins, comprising contacting a chlorofluoroalkene of the formula $R_fCCl=CClR_f$ wherein each $R_f$ is a perfluoroalkyl group independently selected from the group consisting of $CF_3$, $C_2F_5$, n-$C_3F_7$, i-$C_3F_7$, n-$C_4F_9$, i-$C_4F_9$ and t-$C_4F_9$, with hydrogen in the presence of a catalyst at a temperature sufficient to cause replacement of at least one of the chlorine substituents of the chlorofluoroalkene with hydrogen to produce a product mixture comprising a fluorine-containing olefin of the formula E- or Z-$R^1CH=CHR^2$, wherein each of $R^1$ and $R^2$ are, perfluoroalkyl groups independently selected from the group consisting of $CF_3$, $C_2F_5$, n-$C_3F_7$, i-$C_3F_7$, n-$C_4F_9$, i-$C_4F_9$ and t-$C_4F_9$, wherein said catalyst is a composition comprising chromium and nickel.

2. The process of claim 1 wherein said catalyst is a composition comprising from about 10% to about 90% chromium and from about 90% to about 10% nickel.

3. The process of claim 1, wherein the catalyst composition further comprises an alkali metal selected from potassium and cesium and rubidium.

4. The process of claim 3, wherein said alkali metal is from 1 to 30 weight percent.

5. The process of claim 1, wherein said catalyst is on a support.

6. The process of claim 5, wherein said support is a metal fluoride, alumina or titania.

7. The process of claim 6, wherein said metal fluoride is a selected from magnesium fluoride, calcium fluoride, strontium fluoride and barium fluoride.

8. A process for the preparation of fluorine-containing alkynes, comprising contacting a chlorofluoroalkene of the formula $R_fCCl=CClR_f$ wherein each $R_f$ is a perfluoroalkyl group independently selected from the group consisting of $CF_3$, $C_2F_5$, n-$C_3F_7$, i-$C_3F_7$, n-$C_4F_9$, i-$C_4F_9$ and t-$C_4F_9$ with hydrogen in the presence of a catalyst at a temperature sufficient to cause elimination of the chlorine substituents of the chlorofluoroalkene to produce a fluorine-containing alkyne of the formula $R^1\equiv CR^2$, wherein each of $R^1$ and $R^2$ are, perfluoroalkyl groups independently selected from the group consisting of $CF_3$, $C_2F_5$, n-$C_3F_7$, i-$C_3F_7$, n-$C_4F_9$, i-$C_4F_9$ and t-$C_4F_9$, wherein said catalyst is a composition comprising copper and nickel.

9. The process of claim 8, wherein the catalyst composition further comprises an alkali metal selected from potassium, cesium and rubidium.

10. The process of claim 9, wherein the catalyst composition further comprises chromium.

11. The process of claim 10, wherein said alkali metal is present in from 1 to about 30 weight percent.

12. The process of claim 8, wherein said catalyst is on a support.

13. The process of claim 12, wherein said support is a metal fluoride, alumina or titania.

14. The process of claim 8, wherein the ratio of hydrogen to chlorofluoroalkene is from about 1:1 to about 5:1.

15. The process of claim 8, wherein the process is conducted at a temperature of at least 350° C.

16. The process of claim 1, wherein the product mixture further comprises a chlorofluoroalkene where one of the chlorine atoms has been replaced by hydrogen.

17. The process of claim 1, wherein each $R_f$ is $CF_3$ and the product mixture further comprises E and/or Z-2-chloro-1,1,1,4,4,4-hexafluoro-2-butene.

18. The process of claim 1, wherein each $R_f$ is $CF_3$ and the product mixture further comprises Z-2-chloro-1,1,1,4,4,4-hexafluoro-2-butene.

19. A process for the preparation of fluorine-containing olefins comprising contacting a chlorofluoroalkene having the formula $CF_3CCl=CClCF_3$ with hydrogen in the presence of a catalyst at a temperature sufficient to cause replacement of at least one of the chlorine substituents of the chlorofluoroalkene with hydrogen to produce a product mixture comprising E and/or Z-2-chloro-1,1,1,4,4,4-hexafluoro-2-butene.

20. The process of claim 19, wherein said product mixture further comprises E and/or Z $CF_3CH=CHCF_3$.

* * * * *